United States Patent [19]

LeBoeuf

[11] 4,396,583
[45] Aug. 2, 1983

[54] DEVICE FOR SINGLE SOLUTION CONTACT LENS STERILIZATION

[75] Inventor: Albert R. LeBoeuf, Sturbridge, Mass.

[73] Assignee: American Optical Corporation, Southbridge, Mass.

[21] Appl. No.: 292,760

[22] Filed: Aug. 14, 1981

[51] Int. Cl.³ .............................................. A61L 2/18
[52] U.S. Cl. .................................... 422/301; 206/5.1; 220/371; 422/30; 422/113; 422/116
[58] Field of Search ................. 422/30, 300, 301, 116, 422/112, 113; 206/5.1, 439, 484.1; 220/367, 371, 373

[56] References Cited

U.S. PATENT DOCUMENTS

| 4,011,941 | 3/1977 | Parsons | 206/5.1 |
| 4,013,410 | 3/1977 | Thomas et al. | 422/30 |
| 4,154,342 | 5/1979 | Wallace | 206/439 |

Primary Examiner—Barry S. Richman
Attorney, Agent, or Firm—Kenway & Jenney

[57] ABSTRACT

A container with a liquid-impervious, vapor-permeable membrane for sterilizing lenses and storing them using the buffered hydrogen peroxide saline solution. The container is also provided with catalytic means to decompose the hydrogen peroxide following termination of the sterilizing period with the membrane permitting escape of the gases produced by the decomposition while preventing passage of liquid therethrough.

7 Claims, 3 Drawing Figures

DEVICE FOR SINGLE SOLUTION CONTACT LENS STERILIZATION

BACKGROUND OF THE INVENTION

The present invention is directed to sterilizing contact lenses. More particularly, the present invention is directed to a device particularly suitable for sterilizing and storing contact lenses.

U.S. Pat. No. 3,912,451 discloses the suitability of hydrogen peroxide for sterilizing contact lenses and a catalyst, presumably platinum black, for decomposing the hydrogen peroxide following sterilization and a saline hydrogen peroxide solution suitable for such use.

U.S. Pat. No. Des. 242,265 discloses a design of a plastic support for a platinum black catalyst useful in practicing the decomposition of hydrogen peroxide according to the teaching of U.S. Pat. No. 3,912,451.

U.S. Pat. No. 4,011,941 discloses a capsule designed for holding contact lenses during hydrogen peroxide sterilization which permits the lenses to be sterilized in a single container.

SUMMARY OF THE INVENTION AND BRIEF DESCRIPTION OF THE DRAWINGS

A device having a vapor permeable, liquid impermeable barrier permits sterilization of contact lenses with a single solution of saline containing hydrogen peroxide. The barrier may be of any suitable material having a porosity which does not cause a buildup of pressure as the hydrogen peroxide decomposes during or after sterilization while prohibiting passage of liquid therethrough. Hydrophobic barriers are preferred since they are most effective in the sterilizing liquid transfer while providing a maximum pore size.

DESCRIPTION OF THE PREFERRED EMBODIMENTS

Figure 1:
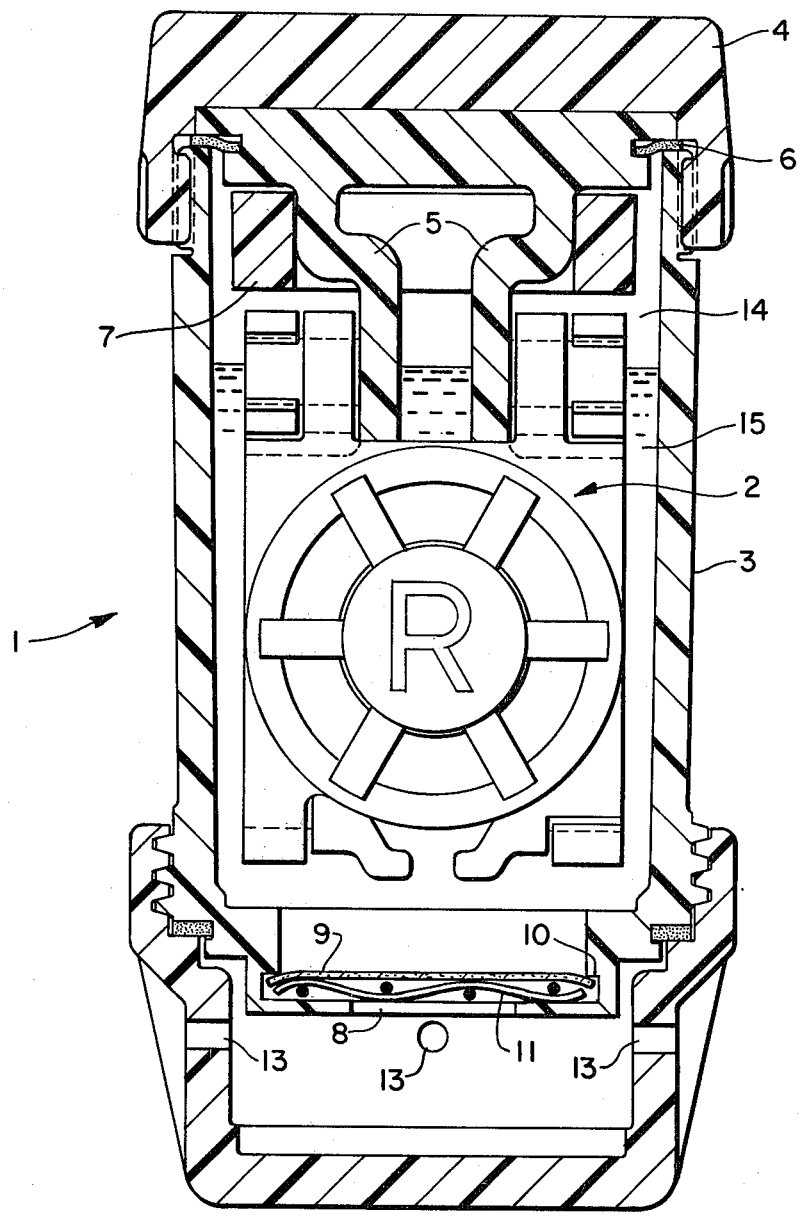
FIG. 1 is one embodiment shown in cross-section.

Referring to FIG. 1, contact lens sterilization apparatus 1 shown generally has a pair of baskets 2 (one shown) for supporting contact lenses (not shown). Body 3 has a threadable attached cap 4 with a pair of elongated members 5 connecting baskets 2 to cap 4. Ring gasket 6 provides a liquid and gas seal between body 3 and cap 4. A suitable basket arrangement is shown in U.S. Pat. No. 3,770,113. A catalyst-covered member 7 is supported by friction engagement with elongated members 5. An external configuration as shown in U.S. Pat. No. Des. 242,265 is preferred. The distal end of body 3 has an opening 8 which acts as a passage between the apparatus interior and the surrounding atmosphere. A hydrophobic silicone membrane 9 having a thickness of 0.8 millimeters and made of a General Electric RTV silicone rubber is held in place by lip 10 and is supported by wire mesh backing 11. Cover 12 protects the vapor-permeable, liquid-impermeable barrier structure 9 and has unrestricted passages 13. Another suitable barrier material which may be substituted for silicone membrane 9 is a bacteriological filter material sold under the tradename ACRODISC TF Teflon. This material is a Teflon film bonded to polypropylene of about 175 microns in in thickness and with about a 0.2 micron pore size. Cavity 14 is partially filled with a saline-hydrogen peroxide solution 15. After an appropriate period of sterilization, apparatus 1 is inverted and catalyst-covered member 7 is brought into contact with solution 15 causing decomposition of the hydrogen peroxide. Inversion of apparatus 1 may be by manual or mechanical means. For example, a device of the type shown in U.S. Pat. No. 4,143,116 may be used.

Figure 2:
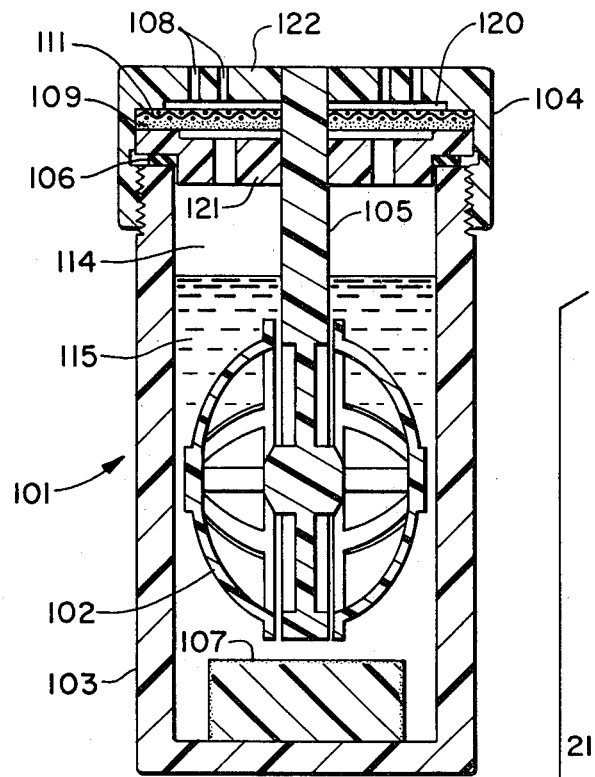
FIG. 2 is a front view of a another embodiment of the present invention shown in cross-section.

Referring to FIG. 2, baskets 102 are supported from cap 104 by elongated member 105. Ring gasket 106 is used to seal cap 104 to body 103. Catalyst covered member 107 is located in the bottom of body 103. Cap 104 has a cavity 120 between porous plate 121 and top 122. ACRODISC member 109 and wire mesh backing 111 are retained in cavity 120. Openings 108 allow gases passing through membrane 109 to enter the surrounding atmosphere. In use, cavity 114 is partially filled with saline-hydrogen peroxide solution 115. Although the hydrogen peroxide begins decomposition immediately, its concentration is reduced at a rate which permits sterilization of the contact lenses contained in baskets 102 prior to reaching a level at which further sterilization does not take place. This device offers the advantage that it is unnecessary for the user to invert apparatus 101 manually or with the assistance of some mechanical device.

Figure 3:
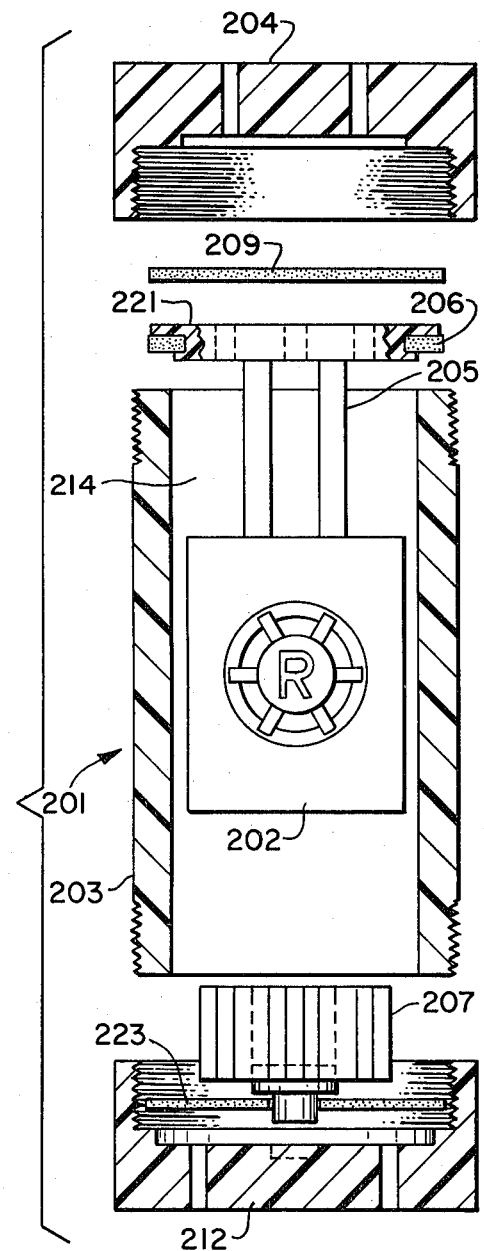
FIG. 3 is a front view of a third embodiment of the present invention shown in exploded cross-section.

Referring to FIG. 3, baskets 202 are supported from cap 204 by plate 221 and elongated members 205. Porous plate 221 carries gasket 206 and supports ACRODISC membrane 209 between it and cap 204. A similar membrane 223 is located between cover 212 and catalyst member 207. In such a device, cavity 214 prevents any pressure buildup regardless of the orientation of apparatus 201.

I claim:

1. A container for sterilizing and storing contact lenses comprising:
   a pair of lens-holding baskets,
   a hollow cylindrical body, said body being wide enough to hold said pair of lens-holding baskets, said body having a first opening at one end which is wide enough so that said pair of lens-holding baskets can pass therethrough and having a second opening at the other end thereof which acts as a passage between the interior of said container and the outside ambient atmosphere, said body further comprising a vapor-permeable housing for supporting a vapor-permeable, liquid-impermeable barrier, said housing located adjacent to said second opening, said housing with said barrier therein sealing said second opening to prevent passage of liquid therethrough while permitting passage of gas therethrough, said barrier further supported in said housing by a vapor-permeable support means,
   a first cap, said cap containing a pair of elongated members to which said pair of lens-holding baskets is attached, said cap serving as a closure means for said first opening,
   a second cap having unrestricted passages from the interior of said cap to the exterior to permit escape of the gas passing through the barrier, said cap serving as a closure means for said second opening,
   a catalyst-covered member frictionally supported in said container by said elongated members.

2. A container for sterilizing and storing contact lenses comprising:
   a pair of lens-holding baskets, a hollow cylindrical body having a first closed end and a second open end, said open end being wide enough so that said pair of lens-holding baskets can pass therethrough, a catalyst-covered member positioned in said hollow cylindrical body so that said catalyst member is in an abutting relationship with said closed end of said body, a cap having an elongated member which supports said lens-holding baskets, said cap also having a centrally located cavity, said cavity containing a vapor-permeable, liquid-impermeable barrier and a vapor-permeable support means for securely bracing said vapor-permeable, liquid-impermeable barrier, said barrier being positioned by said support means therefor to seal said open end to prevent passage of liquid therethrough while permitting passage of gas therethrough, said cap further including a number of passages connecting the interior of said cap with the surrounding atmosphere to permit escape of the gas passing through the barrier.

3. A container for sterilizing and storing contact lenses comprising:

a pair of lens-holding baskets, a hollow cylindrical body having a first and second open end, said first end being wide enough so that said pair of lens-holding baskets can pass therethrough, and said second open end being wide enough so that a catalyst-covered member can pass therethrough, a first cap for closing said first open end, a porous plate inserted in said first cap, said porous plate containing two elongated members, said elongated members supporting said pair of lens-holding baskets, said first cap further comprising a vapor-permeable, liquid-impermeable barrier inserted in said first cap between the interior surface of said cap and said porous plate, said barrier sealing said first open end to prevent passage of liquid therethrough while permitting passage of gas therethrough, said first cap having passages from the interior of the cap to the outside ambient atmosphere, to permit escape of the gas passing through the barrier, a second cap for closing said second open end, said second cap supporting said catalyst member, said second cap further comprising a porous membrane inserted in said second cap between said catalyst and the interior surface of said second cap, said porous membrane sealing said second open end to prevent passage of liquid therethrough while permitting passage of gas therethrough, said second cap having passages from the interior of said cap to the outside ambient atmosphere to permit escape of the gas passing through said porous membrane.

4. The container of claim 1, 2, or 3 wherein said barrier is a silicone membrane.

5. The container of claim 1, 2, or 3 wherein said barrier is a micro-biological filter.

6. The container of claim 1, 2, or 3 wherein said barrier is a hydrophobic membrane.

7. The container of claim 1, 2, or 3 wherein said barrier has a pore size of about 0.2 microns.

* * * * *